US012778980B2

(12) United States Patent
Guo et al.

(10) Patent No.: US 12,778,980 B2
(45) Date of Patent: Nov. 3, 2026

(54) PEGYLATED RAPAMYCIN COMPOUND AND PREPARATION METHOD THEREFOR AND APPLICATION THEREOF

(71) Applicants: HANGZHOU YISHENG PHARMACEUTICAL TECHNOLOGY DEVELOPMENT CO., LTD, Zhejiang (CN); SHENYANG SUNSHINE PHARMACEUTICAL CO., LTD., Liaoning (CN)

(72) Inventors: Shengrong Guo, Hangzhou (CN); Yuanyuan Shen, Hangzhou (CN)

(73) Assignees: HANGZHOU YISHENG PHARMACEUTICAL TECHNOLOGY DEVELOPMENT CO., LTD, Zhejiang (CN); SHENYANG SUNSHINE PHARMACEUTICAL CO., LTD., Liaoning (CN)

( * ) Notice: Subject to any disclaimer, the term of this patent is extended or adjusted under 35 U.S.C. 154(b) by 471 days.

(21) Appl. No.: 18/252,309

(22) PCT Filed: Mar. 30, 2022

(86) PCT No.: PCT/CN2022/083907
§ 371 (c)(1),
(2) Date: May 9, 2023

(87) PCT Pub. No.: WO2022/206796
PCT Pub. Date: Oct. 6, 2022

(65) Prior Publication Data
US 2024/0009228 A1 Jan. 11, 2024

(30) Foreign Application Priority Data
Apr. 2, 2021 (CN) ......................... 202110365285.9

(51) Int. Cl.
*A61K 31/787* (2006.01)
*A61K 9/19* (2006.01)
(Continued)

(52) U.S. Cl.
CPC .............. *A61K 31/787* (2013.01); *A61K 9/19* (2013.01); *A61K 31/436* (2013.01); *A61K 45/06* (2013.01); *B82Y 5/00* (2013.01); *B82Y 30/00* (2013.01)

(58) Field of Classification Search
None
See application file for complete search history.

(56) References Cited

U.S. PATENT DOCUMENTS

2016/0271116 A1 9/2016 Jia et al.
2019/0255189 A1 8/2019 Huang et al.
2021/0023232 A1 1/2021 Wang et al.

FOREIGN PATENT DOCUMENTS

CN 104448295 A 3/2015
CN 104689330 A * 6/2015
(Continued)

OTHER PUBLICATIONS

Kishimoto TK, et al.; "Improving the efficacy and safety of biologic drugs with tolerogenic nanoparticles"; Nature Nanotechnology, Oct. 2016; pp. 890-899, vol. 11, Macmillan Publishers Limited.
(Continued)

*Primary Examiner* — Robert A Wax
*Assistant Examiner* — Andre Mach
(74) *Attorney, Agent, or Firm* — MUNCY, GEISSLER, OLDS & LOWE, P.C.

(57) ABSTRACT

A PEGylated rapamycin compound and a preparation method therefor and an application thereof. The compound is represented by Formula (I), wherein n is 10-150. The preparation method is as follows: mPEG-COOH is dissolved in an organic solvent, catalysts EDC·HCl and DMAP, and RAPA are added, and the reaction is performed by stirring at 0-40° C. in the dark. An application of the compound and pharmaceutical preparations thereof in the preparation of a drug for reducing immune response can effectively inhibit the production of anti-drug antibodies of biological drugs such as urate oxidase, has good clinical application prospects, and is especially suitable to be prepared into a nano-drug.

Formula (I)

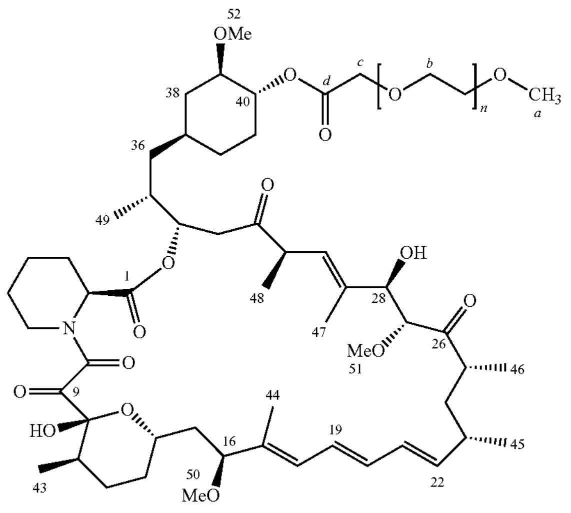

1 Claim, 7 Drawing Sheets

(51) Int. Cl.

| | |
|---|---|
| ***A61K 31/436*** | (2006.01) |
| ***A61K 45/06*** | (2006.01) |
| ***B82Y 5/00*** | (2011.01) |
| ***B82Y 30/00*** | (2011.01) |

(56) References Cited

FOREIGN PATENT DOCUMENTS

| | | | | | |
|---|---|---|---|---|---|
| CN | 110314236 | A | | 10/2019 | |
| JP | 2009529050 | A | | 8/2009 | |
| JP | 2015078247 | A | | 4/2015 | |
| JP | 2018012694 | A | | 1/2018 | |
| WO | WO2007103348 | A2 | | 9/2007 | |
| WO | WO-2018053434 | A1 | * | 3/2018 | .............. A61P 35/00 |

OTHER PUBLICATIONS

Tam, Yu Tong et al. "Oligo(Lactic Acid)8-Rapamycin Prodrug-Loaded Poly(Ethylene Glycol)-block-Poly(Lactic Acid) Micelles for Injection." Pharmaceutical Research 36 (2019): 10 pages.

* cited by examiner

| H | δ |
|---|---|
| a | 4.09 |
| b | 3.43-3.80 |
| c | 3.31 |

| C | δ |
|---|---|
| a | 67.93 |
| b | 68.44-69.85 |
| c | 58.04 |

PEGYLATED RAPAMYCIN COMPOUND AND PREPARATION METHOD THEREFOR AND APPLICATION THEREOF

FIELD OF THE INVENTION

The invention belongs to the technical field of biomedicine, in particular, to a PEGylated rapamycin compound and a preparation method therefor and an application thereof.

BACKGROUND OF THE INVENTION

In 2018, 8 of the TOP 10 drugs with the largest sales and sales growth in the world are monoclonal antibodies. The global biopharmaceutical industry is growing rapidly. Compared with small-molecule drugs, most biological drugs are immunogenic, and they will cause an immune response and produce anti-drug antibodies after entering the body, thereby neutralizing or changing the pharmacokinetics and biodistribution of biological drugs, and more seriously inducing life-threatening toxic side effects such as hypersensitivity reactions in the body. Therefore, inhibiting the production of antidrug antibodies during the treatment with the biological drugs is critical to improving the safety and efficacy of the biological drugs.

Immunosuppressants refer to drugs that inhibit the immune response of the body. They can inhibit the proliferation and function of cells related to the immune response (macrophages such as T cells and B cells), thereby reducing the antibody immune response. The immunosuppressants are mainly used for organ transplantation to resist rejection and for autoimmune diseases such as rheumatoid arthritis, lupus erythematosus, dermatomycosis, membranous glomerulonephritis, inflammatory bowel disease, and autoimmune hemolytic anemia.

Rapamycin (RAPA), also called sirolimus, is a lipophilic triene nitrogen-containing macrolides antibiotic immunosuppressant produced by *Streptomyces hygroscopicus*, and can be used for adjuvant therapy of cancer, anti-graft rejection and other immune diseases. Rapamycin plays an immunosuppressive role by blocking the signal transduction involved in mammalian target of rapamycin (mTOR), preventing the differentiation of T cells and the maturation of dendritic cells.

Takashi K. Kishimoto first reported that immunosuppressant-rapamycin-loaded poly(lactic acid-co-glycolic acid, PLGA) nanoparticles are immunotolerant, which can effectively inhibit the production of anti-drug antibodies of biological drugs (Nature nanotechnology, 2016, 11(10): 890-899), and defined it as immunotolerant nanoparticles. The above literature reported that rapamycin PLGA nanoparticles prepared by embedding rapamycin on a PLGA carrier have the functions of inducing immune tolerance and inhibiting the production of anti-drug antibodies of biological drugs. PLGA is a synthetic high molecular weight compound, which itself has no pharmacological effect, and is a pharmaceutical excipient product.

BRIEF SUMMARY OF THE DISCLOSURE

A first objective of the invention is to provide a PEGylated rapamycin compound. The compound contains hydrophobic rapamycin moiety and hydrophilic PEG chain, and is a good carrier for the preparation of nanoparticles.

A second objective of the invention is to provide a preparation method for the above compound with mild reaction conditions and simple operations.

A third objective of the invention is to provide an application of the above compound. The compound is prepared into nano-drugs, freeze-dried preparations, pharmaceutical compositions and has a use in preparing drugs used to reduce the immune response.

A PEGylated rapamycin compound represented in formula (I), wherein n is 10-150.

Formula (I)

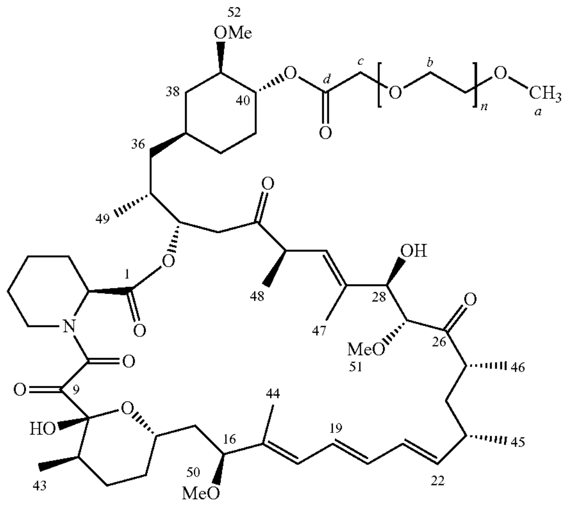

The invention further discloses a preparation method for the above PEGylated rapamycin compound, which includes: dissolving mPEG-COOH in an organic solvent, adding catalysts EDC-HCl, DMAP and RAPA, and performing the reaction by stirring at 0-40° C. in the dark.

In an embodiment of the invention, a reaction temperature of the preparation method is preferably 20~30° C.

In an embodiment of the invention, the organic solvent is one or both of dichloromethane and chloroform, preferably dichloromethane.

In an embodiment of the invention, a molar ratio of the mPEG-COOH to the RAPA is 5:1~1:5, preferably 3:1-1:3.

In an embodiment of the invention, the preparation method further includes a separation and purification step after the reaction, wherein the separation and purification step is dialysis purification or silica gel column chromatography.

In an embodiment of the invention, the dialysis purification uses a dialysis bag and a dialysis solvent for separation and purification. A molecular weight cutoff of the dialysis bag is 500-5000, preferably 1500. The dialysis solvent is one or more of DMSO, halogenated hydrocarbon, tetrahydrofuran and ultrapure water, preferably one or both of DMSO and ultrapure water, more preferably DMSO and ultrapure water.

In an embodiment of the invention, an elution mode of silica gel column chromatography is isocratic elution or gradient elution, preferably gradient elution.

In an embodiment of the invention, an eluent used in the gradient elution is two or more of dichloromethane, ethyl acetate and anhydrous methanol, preferably a mixed solvent of dichloromethane and anhydrous methanol. A ratio of dichloromethane to anhydrous methanol (v/v) is 100:1-10:1, preferably 50:1-20:1.

The invention further discloses a nano-drug, which includes the PEGylated rapamycin compound in an effective drug loading, preferably consisting of the PEGylated rapamycin compound in an effective drug loading and a free rapamycin.

In an embodiment of the invention, a particle size of the PEGylated rapamycin nanoparticle is 5-1000 nm, preferably 50-200 nm.

In an embodiment of the invention, a drug loading of the PEGylated rapamycin nanoparticle is 15%-100%, preferably 25%-85%.

The invention further discloses a preparation method for the nano-drug, which is prepared by a bottom-up approach. The preparation method for the PEGylated rapamycin nanoparticle includes emulsification/solvent evaporation, nanoprecipitation, thin film dispersion, self-assembly or SPG membrane emulsification, preferably emulsification/solvent evaporation.

In an embodiment of the invention, the emulsification/solvent evaporation includes: dissolving the PEGylated rapamycin compound or dissolving the PEGylated rapamycin compound and the rapamycin in an organic solvent to form an organic phase, which are then added to an aqueous phase containing polyvinyl alcohol to prepare an oil-in-water emulsion by high-speed stirring, sonication, vortexing and/or using a high-pressure homogenizer, and finally obtaining a PEGylated rapamycin nanoparticle solution by evaporating and removing the organic solvent.

In an embodiment of the invention, an organic solvent used in the emulsification/solvent evaporation is one or both of chloroform and $CH_2Cl_2$, preferably $CH_2Cl_2$.

In an embodiment of the invention, a concentration of the PEGylated rapamycin in the emulsification/solvent evaporation is 0.1-10 mg/mL in the organic phase, preferably 0.5-5 mg/mL.

In an embodiment of the invention, the emulsification/solvent evaporation further includes the free rapamycin, and a ratio of the free rapamycin to the PEGylated rapamycin is 0-20/1 (w/w), preferably 1/5-5/1 (w/w).

In an embodiment of the invention, a ratio of the organic phase to the aqueous phase in the emulsification/solvent evaporation is 1/1-1/100 (v/v), preferably 1/2-1/10 (v/v).

In an embodiment of the invention, a concentration of the polyvinyl alcohol in the emulsification/solvent evaporation is 0-5% (w/v) in the aqueous phase, preferably 0.5%-2% (w/v).

The invention further discloses a freeze-dried preparation, which is prepared by freeze-drying an aqueous solution of the PEGylated rapamycin nanoparticle and a freeze-drying protective agent.

In an embodiment of the invention, the freeze-drying protective agent is one or more of sucrose, lactose, mannitol, glucose, trehalose and maltose.

In an embodiment of the invention, a concentration of the freeze-drying protective agent in aqueous solution of the PEGylated rapamycin nanoparticle is 0.1%-20% (w/v), preferably 2%-8% (w/v).

In an embodiment of the invention, a pre-freezing temperature used in preparing the freeze-dried preparation is lower than −10° C., preferably −30° C.-−50° C. The pre-freezing methods are fast freezing and slow freezing, preferably fast freezing.

The invention further discloses a pharmaceutical composition, which includes a therapeutically effective dose of the PEGylated rapamycin compound and a pharmaceutically acceptable carrier.

In an embodiment of the invention, a biological drug is further included.

In an embodiment of the invention, the biological drug is a protein and polypeptide drug, one or more of urate oxidase, enzymes and coenzyme drugs, nucleic acid and degradation products and derivatives thereof, cell growth factors or cytokines, preferably urate oxidase.

The invention further discloses an application of the PEGylated rapamycin compound, the nano-drug, the freeze-dried preparation or the pharmaceutical composition in preparing a drug for reducing an immune response.

Compared with the conventional art, the present invention has the following beneficial effects:

1. In the invention, the PEGylated rapamycin compound has a clear structural composition and a high purity, with suitable hydrophobic rapamycin ends and hydrophilic PEG chain ends, so as to be a good carrier for the preparation of nanoparticles.
2. In the invention, the PEGylated rapamycin nanoparticle consists of the PEGylated rapamycin and rapamycin, with the PEGylated rapamycin also as the carrier; the rapamycin moiety in the PEGylated rapamycin molecule and the free rapamycin molecule constitute the hydrophobic core of the nanoparticle; there are hydrophilic PEG segments on the surface of the nanoparticle, which have high dispersion stability in water.
3. In the invention, the PEGylated rapamycin nanoparticle has immune targeting properties, which may enrich and release drugs in immune organs such as the spleen, effectively inhibit the production of anti-drug antibodies of biological drugs, and generate immune tolerance; in the invention, the content of the rapamycin in the PEGylated rapamycin nanoparticle is high, which has a better effect on inhibiting the production of anti-drug antibodies than rapamycin PLGA nanoparticles while avoiding the toxic and side effects caused by long-term multi-dose administration of rapamycin, and does not contain PLGA and other pharmaceutical excipients.

In the invention, an amphiphilic PEGylated rapamycin is prepared by linking hydrophilic polyethylene glycol to hydrophobic rapamycin by esterification, and then the PEGylated rapamycin alone or the PEGylated rapamycin together with rapamycin are used to prepare the PEGylated rapamycin nanoparticle with good water solubility, so that the invention may be effectively used for inhibiting the production of anti-drug antibodies of biological drugs such as urate oxidase and the like, and has a good clinical application prospect.

DETAILED DESCRIPTION OF THE INVENTION

Figures 1A, 1B:
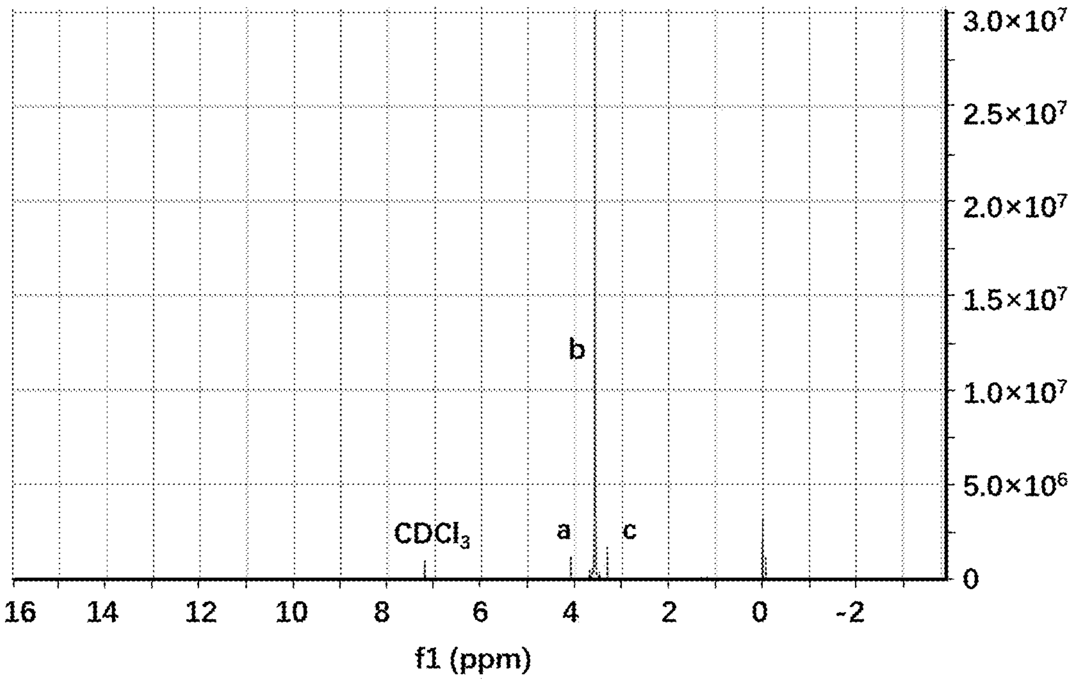
FIGS. 1(*a*)-1(*e*) show $^1$H and $^{13}$C NMR spectrums of the mPEG-COOH ($CDCl_3$ is the solvent), wherein FIG. 1(*a*) is a full diagram of the $^1$H NMR spectrum, FIG. 1(*b*) shows an assignment of each peak on the $^1$H NMR spectrum, FIG. 1(*c*) is a full diagram of the $^{13}$C NMR spectrum, FIG. 1(*d*) is a partial enlarged diagram of the $^{13}$C NMR spectrum, and FIG. 1(*e*) shows an assignment of each peak on the $^{13}$C NMR spectrum of ($CDCl_3$ is the solvent)
Figure 1C:
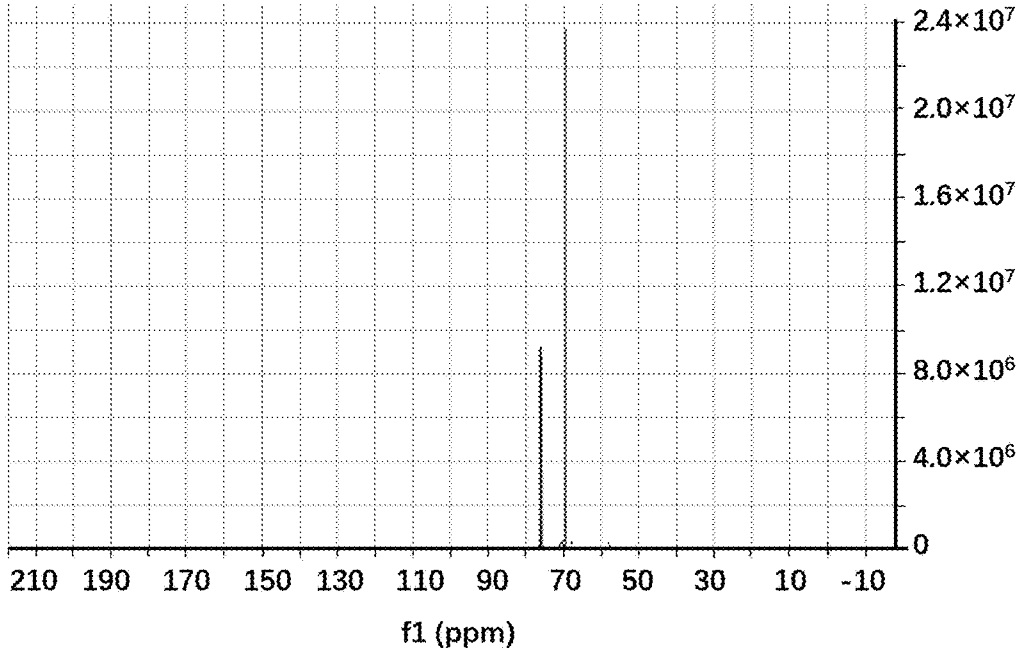
Figure 1D:
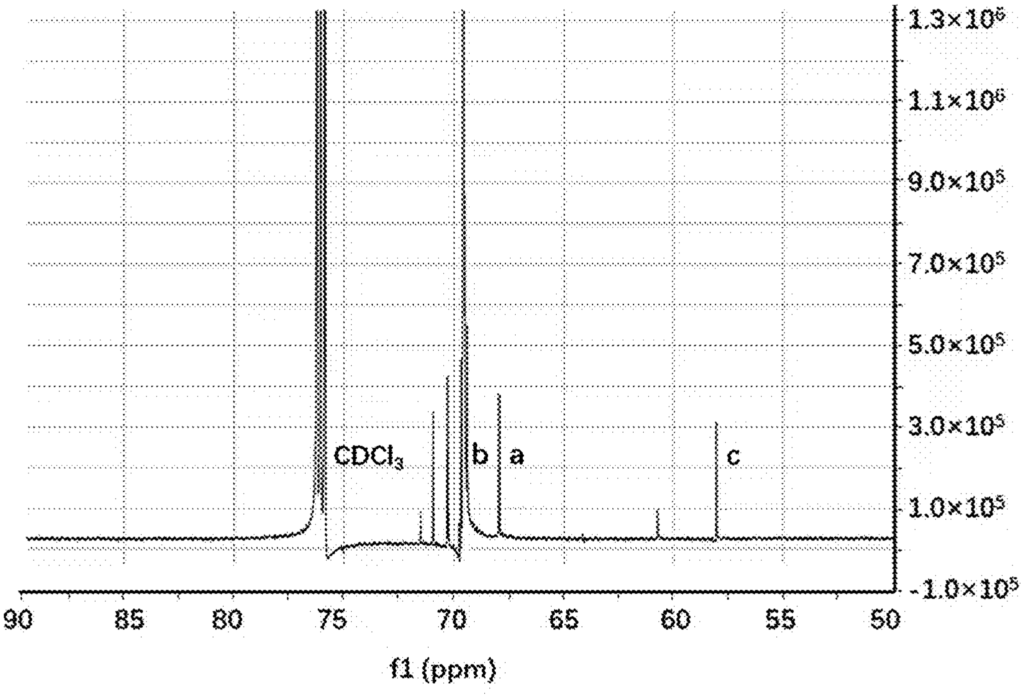
Figures 1E, 2A:
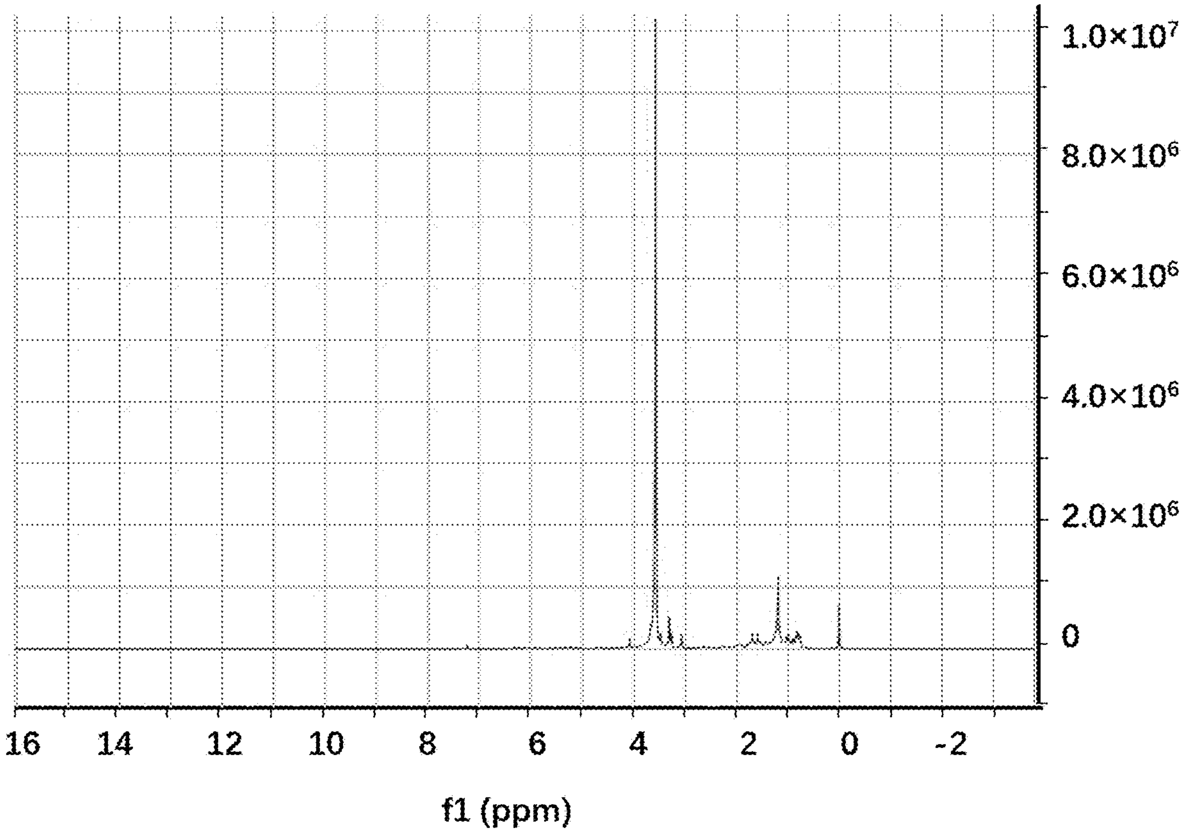
FIGS. 2(*a*)-2(*h*) show $^1$H and $^{13}$C NMR spectrums of the PEGylated rapamycin ($CDCl_3$ is the solvent), wherein FIG. 2(*a*) is a full diagram of the $^1$H NMR spectrum, FIGS. 2(*b*) to 2(*c*) are partial enlarged diagrams of the $^1$H NMR spectrum, FIG. 2(*d*) is a full diagram of the $^{13}$C NMR spectrum, and FIGS. 2(*e*) to 2(*h*) are partial enlarged diagrams of the $^{13}$C NMR spectrum.
Figure 2B:
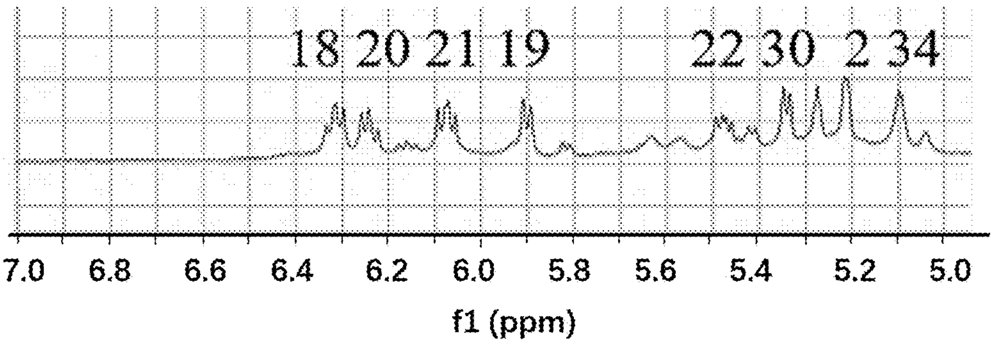
Figure 2C:
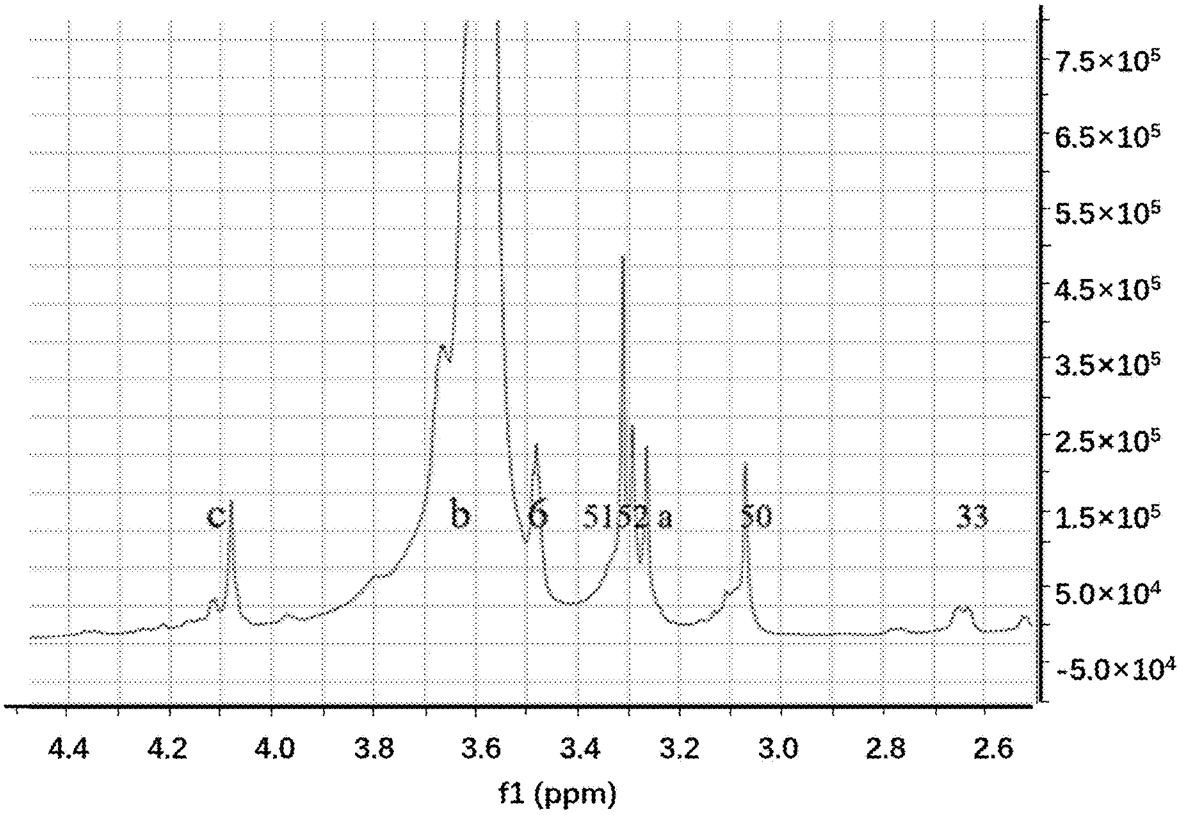
Figure 2D:
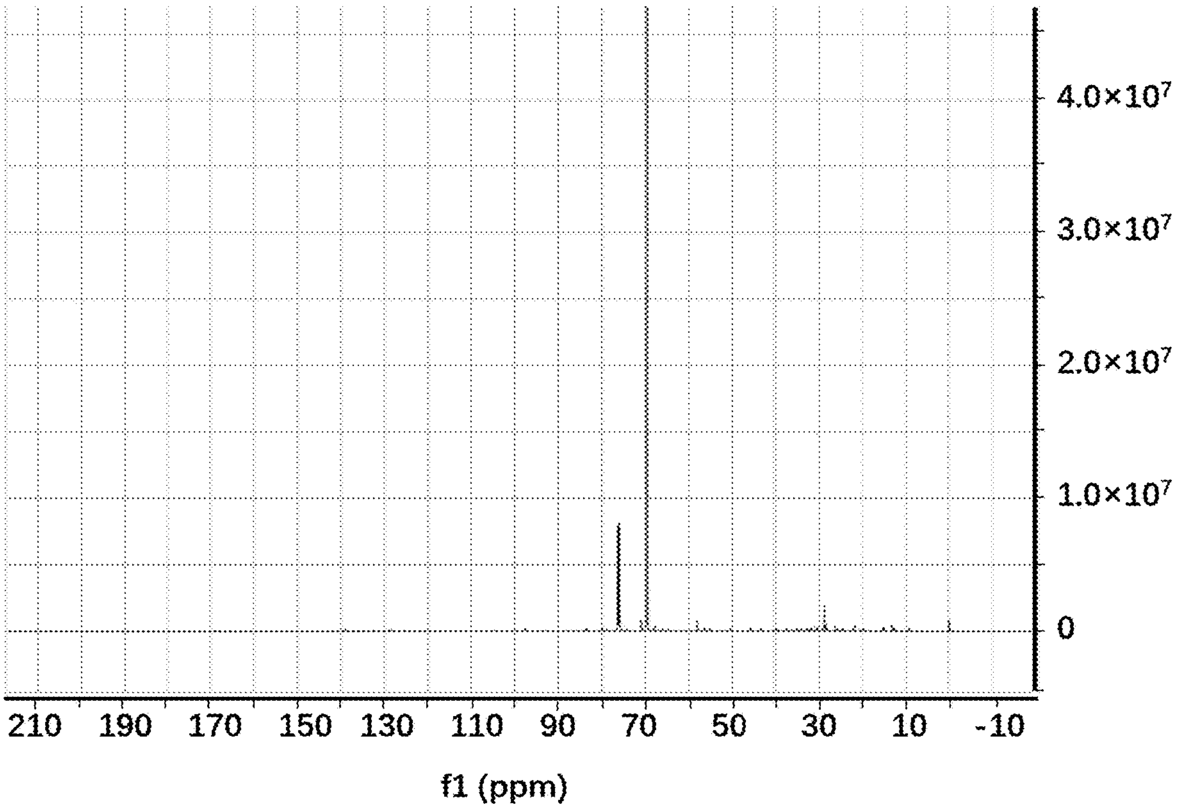
Figure 2E:
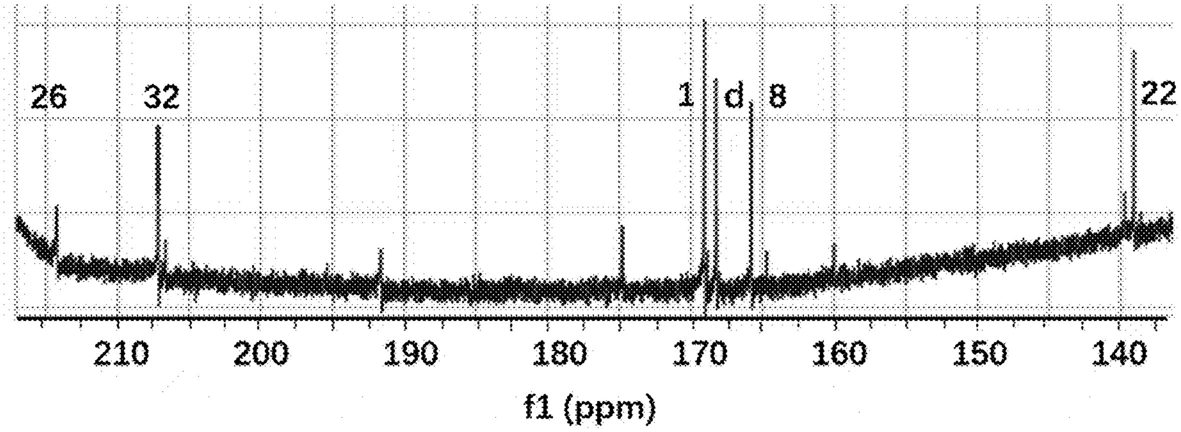
Figure 2F:
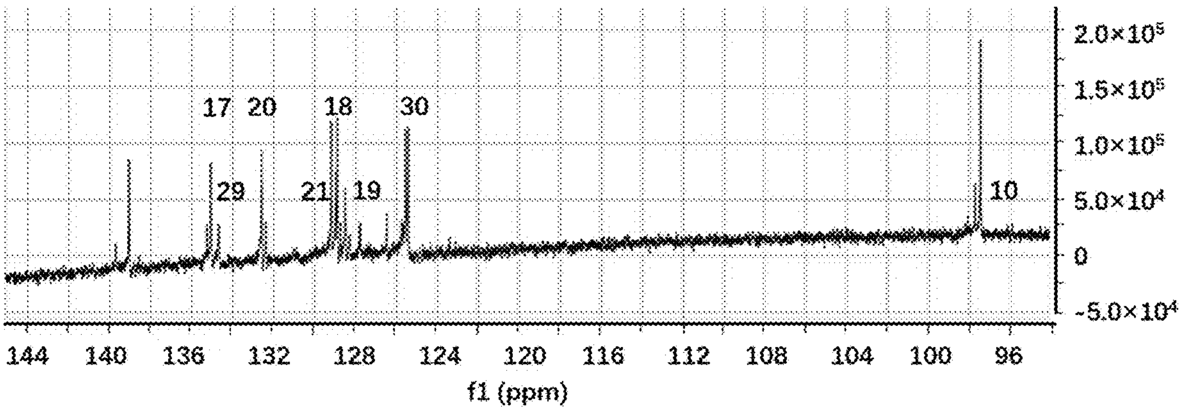
Figure 2G:
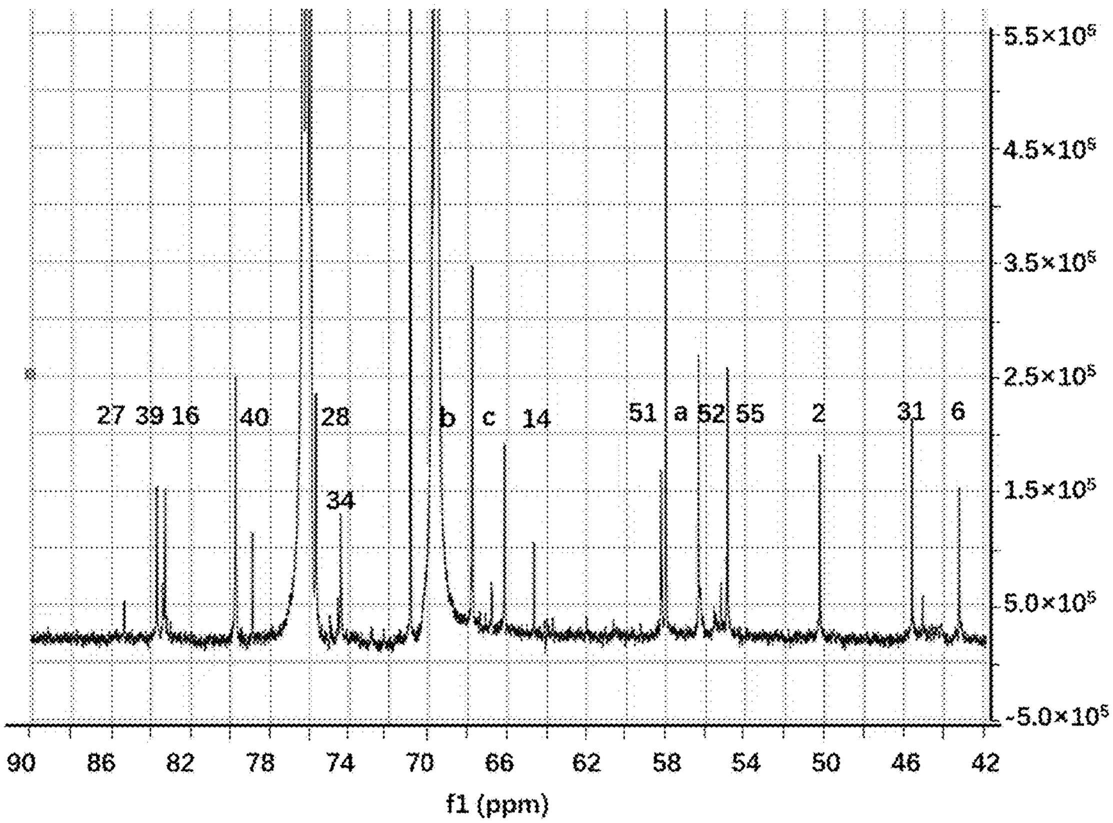
Figure 2H:
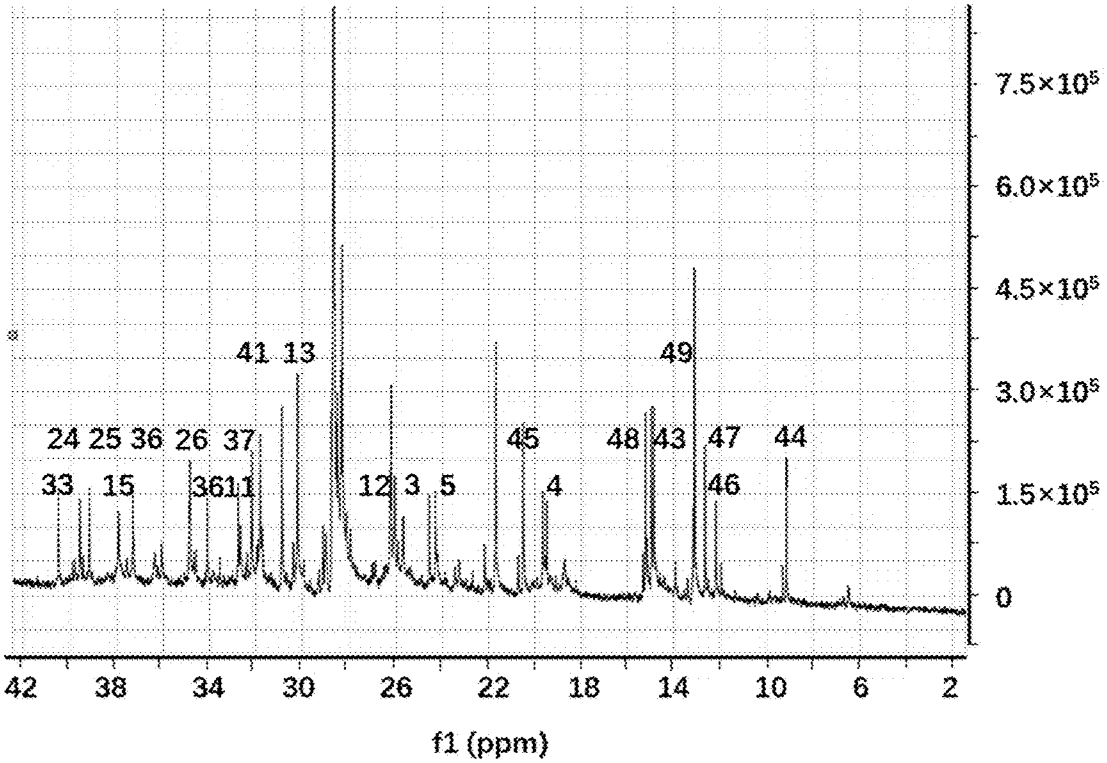

The following further describes the present invention in combination with specific embodiments. It should be understood that these embodiments are only used for illustrating the present invention, but not for the limitation of the scope of the present invention. Improvements and adjustments made by those skilled in the art according to the invention in practical applications still belong to the protection scope of the invention.

The raw materials, reagents, instruments, etc. used in the invention may be purchased through commercial channels. The abbreviated terms involved are as follows: EDC·HCl: 1-ethyl-(3-dimethylaminopropyl)carbodiimide hydrochloride; DMAP: dimethylaminopyridine; DMSO: dimethyl sulfoxide; PVA: polyvinyl alcohol; DLS: dynamic light scattering.

1. Preparation and Purification of PEGylated Rapamycin

Embodiment 1 mPEG-COOH (PEG for short, with an average molecular weight of about 2000, 0.2 g, 0.1 mmol) is dissolved in $CH_2Cl_2$ (8 mL), and then RAPA (0.1 g, 0.1 mmol), EDC·HCl (0.04 g, 0.2 mmol) and DMAP (0.024 g, 0.2 mmol) are added for oscillating/stirring to be fully dissolved; then the reaction is performed in the dark at room temperature for 36 hours, and a reaction solution is concentrated to obtain a concentrated solution, which is dissolved in DMSO (2 mL) to obtain a solution; the solution is placed in a dialysis bag (molecular weight cut-off: 1500 Da), dialyzed with DMSO and ultrapure water for 1 d and 2 d respectively while changing a dialysis medium every 4 h; finally, a dialysate is freeze-dried to obtain the PEGylated rapamycin of 0.074 g with a yield of 23.2%.

Embodiment 2 mPEG-COOH (PEG for short, with an average molecular weight of about 2000, 0.3007 g, 0.15 mmol) is dissolved in $CH_2Cl_2$ (50 mL), and then RAPA (0.2722 g, 0.30 mmol), EDC·HCl (0.0289 g, 0.15 mmol) and DMAP (0.0020 g, 0.15 mmol) are added for oscillating/stirring to be fully dissolved; then the reaction is performed in the dark at room temperature for 8 hours, and a reaction solution is concentrated to obtain a concentrated solution containing the PEGylated rapamycin with a crude yield of 12.1%.

Embodiment 3 mPEG-COOH (PEG for short, with an average molecular weight of about 2000, 1.196 g, 0.60 mmol) is dissolved in $CH_2Cl_2$ (50 mL), and then RAPA (0.2754 g, 0.30 mmol), EDC·HCl (0.1157 g, 0.60 mmol) and DMAP (0.0070 g, 0.06 mmol) are added for oscillating/stirring to be fully dissolved; then the reaction is performed in the dark at room temperature for 4 hours, and a reaction solution is concentrated to obtain a concentrated solution containing the PEGylated rapamycin with a crude yield of 39.8%.

Embodiment 4 mPEG-COOH (PEG for short, with an average molecular weight of about 2000, 1.8027 g, 0.90 mmol) is dissolved in $CH_2Cl_2$ (20 mL), and then RAPA (0.2758 g, 0.30 mmol), EDC·HCl (0.1727 g, 0.90 mmol) and DMAP (0.0114 g, 0.90 mmol) are added for oscillating/stirring to be fully dissolved; then the reaction is performed in the dark at room temperature for 24 hours, and a reaction solution is concentrated to obtain a concentrated solution containing the PEGylated rapamycin with a crude yield of 59.1%.

Embodiment 5 mPEG-COOH (PEG for short, with an average molecular weight of about 2000, 1.8011 g, 0.90 mmol) is dissolved in $CH_2Cl_2$ (10 mL), and then RAPA (0.2754 g, 0.30 mmol), EDC·HCl (0.1720 g, 0.90 mmol) and DMAP (0.0105 g, 0.09 mmol) are added for oscillating/stirring to be fully dissolved; then the reaction is performed in the dark at room temperature for 18 hours, and a reaction solution is concentrated to obtain a concentrated solution containing the PEGylated rapamycin with a crude yield of 62.1%. The column chromatography is used to purify the concentrated solution containing the PEGylated rapamycin, with a flow shown in Embodiments 6 to 8 as below.

Embodiment 6

In the concentrated solution containing the PEGylated rapamycin, a ratio of each component (PEG-RAPA:RAPA:by-products of PEGylation of rapamycin) is 52:15:9 (w/w); the silica gel column chromatography is used, an eluent is dichloromethane/anhydrous methanol (50:1/30:1/20:1), and an elution time is 25 min/40 min/120 min; a yield of PEG-RAPA is 85.3%, a purity of PEG-RAPA is 95.9%, a removal rate of RAPA is 93.2%, and a removal rate of PEGylated by-products of rapamycin is 90.0%.

Embodiment 7

In the concentrated solution containing the PEGylated rapamycin, a ratio of each component (PEG-RAPA:RAPA:by-products of PEGylation of rapamycin) is 48:13:12 (w/w); the silica gel column chromatography is used, an eluent is dichloromethane/anhydrous methanol (50:1/30:1/10:1), and an elution time is 25 min/50 min/25 min; a yield of PEG-RAPA is 80.8%, a purity of PEG-RAPA is 95.1%, a removal rate of RAPA is 92.8%, and a removal rate of PEGylated by-products of rapamycin is 90.7%.

Embodiment 8

In the concentrated solution containing the PEGylated rapamycin, a ratio of each component (PEG-RAPA:RAPA:by-products of PEGylation of rapamycin) is 41:11:16 (w/w); the silica gel column chromatography is used, an eluent is dichloromethane/anhydrous methanol (50:1/40:1/30:1), and an elution time is 25 min/70 min/200 min; a yield of PEG-RAPA is 63.1%, a purity of PEG-RAPA is 98.5%, a removal rate of RAPA is 96.4%, and a removal rate of PEGylated by-products of rapamycin is 100.0%.

2. Structural Characterization of PEGylated Rapamycin

Embodiment 9

In the invention, a hydroxyl group on the 40th carbon atom on rapamycin molecule and mPEG-COOH with the structure shown in the following formula (II) is subjected to esterification to obtain the PEGylated rapamycin with the structure shown in the following formula (I), wherein the results of the structural characterization are shown in FIGS. 1 and 2.

In FIG. 1, Setting is performed with the peak in the $^1$H NMR spectrum of mPEG-COOH attributed to a hydrogen atom (a) on the methylene group in the —$CH_2$—COOH structure of mPEG-COOH (the peak area is set to 2.00). The peak area corresponding to the hydrogen atom (b) in the repeating structural unit of the mPEG-COOH molecule is 183.86, thereby polymerization degree of mPEG-GOGH is calculated to be 46 and the molecular weight of mPEG-GOGH is 2114.

Combined with the NMR spectra of mPEG-GOGH, rapamycin and PEGylated rapamycin, it is found in FIG. 2 that there is no major change in δ (97.47) for 10-C of rapamycin ( ), there is no major change in δ (75.70) for 28-C of rapamycin, and there is major change in δ (79.31) for 40-C of rapamycin, which show that the PEGylated rapamycin is the product of the esterification between OH linked to 40-C in the rapamycin molecule and mPEG-COOH.

Figure 3:
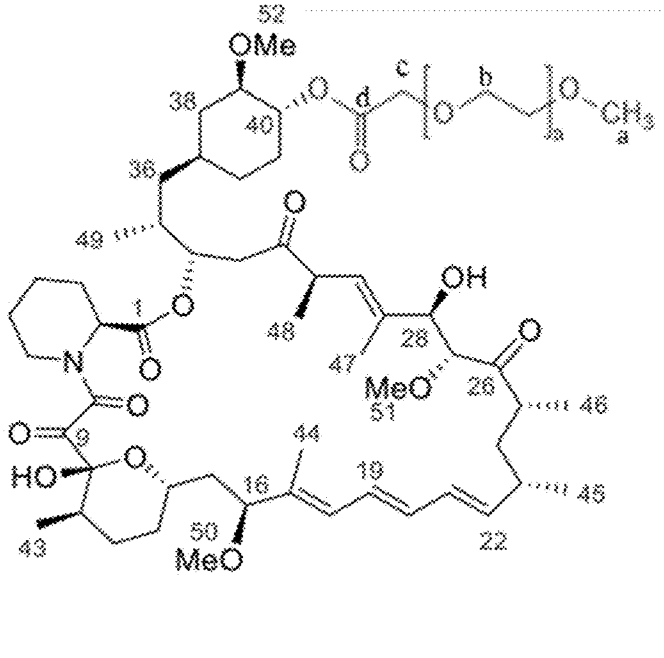
FIG. 3 is a structural formula (I) of the PEGylated rapamycin compound according to the embodiment of the invention.

The molecular structure of the PEGylated rapamycin is shown in FIG. 3:

Formula (I)

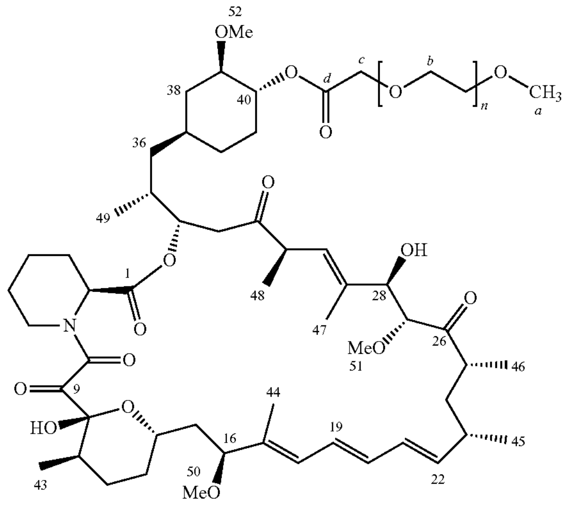

The structural formula of mPEG-COOH is:

Formula (II)

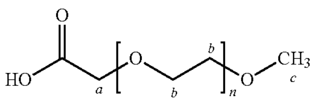

3. Preparation of PEGylated Rapamycin Nanoparticle Solution

Embodiment 10

20 mg PEG-RAPA and 2 mg RAPA are weighed, and added with 5 mL $CH_2Cl_2$ to be fully dissolved to obtain an organic phase; 50 mL of an aqueous solution containing 0.500 PVA is taken as an aqueous phase, and then the organic phase is dripped into the aqueous phase with a syringe while performing ultrasound by using probe ultrasound under ice bath conditions, so as to obtain a white emulsion after performing ultrasonic emulsification for 10 min. The organic solvent is removed by a rotary evaporator at 40° C., and centrifuged at 4000 r/min for 5 min to remove unencapsulated drugs and larger particles for taking a supernatant, so as to obtain the PEGylated rapamycin nanoparticle solution.

A particle size and a polydispersity index (PDI) of the PEGylated rapamycin nanoparticle solution are determined by DLS method.

100 μL PEGylated rapamycin nanoparticle solution is taken, added with acetonitrile until the volume reaches 1 mL, and then is subjected to ultrasound for 20 min to destroy the nanoparticle structure, so that the rapamycin is released free into the solution; then the solution is centrifuged at 12000 r/min for 10 min for taking a supernatant, which is filtered by 0.22 μm microporous membrane; finally, a concentration of RAPA is determined by HPLC analysis, and an encapsulation efficiency and a drug loading of the PEGylated rapamycin nanoparticle are determined.

The test results are shown in Table 1.

TABLE 1

Test Results of PEGylated Rapamycin Nanoparticle

| Particle size (nm) | PDI | Encapsulation efficiency | Drug loading |
|---|---|---|---|
| 70.8 ± 8.8 | 0.243 ± 0.103 | 90.2% | 36.4% |

Embodiment 11

20 mg PEG-RAPA and 4 mg RAPA are weighed, and added with 20 mL $CH_2Cl_2$ to be fully dissolved to obtain an organic phase; 40 mL of an aqueous solution containing 1% PVA is taken as an aqueous phase, and then the organic phase is dripped into the aqueous phase with a syringe while performing ultrasound by using probe ultrasound under ice bath conditions, so as to obtain a white emulsion after performing ultrasonic emulsification for 20 min. The organic solvent is removed by a rotary evaporator at 40° C., and centrifuged at 4000 r/min for 5 min to remove unencapsulated drugs and larger particles for taking a supernatant, so as to obtain the PEGylated rapamycin nanoparticle solution.

The particle size and PDI of the PEGylated rapamycin nanoparticle solution are determined by DLS method.

100 μL PEGylated rapamycin nanoparticle solution is taken, added with acetonitrile until the volume reaches 1 mL, and then is subjected to ultrasound for 20 min to destroy the nanoparticle structure, so that the rapamycin is released free into the solution; then the solution is centrifuged at 12000 r/min for 10 min for taking a supernatant, which is filtered by 0.22 μm microporous membrane; finally, a concentration of RAPA is determined by HPLC analysis, and an encapsulation efficiency and a drug loading of the PEGylated rapamycin nanoparticle are determined.

The test results are shown in Table 2.

TABLE 2

Test Results of PEGylated Rapamycin Nanoparticle

| Particle size (nm) | PDI | Encapsulation efficiency | Drug loading |
|---|---|---|---|
| 104.2 ± 2.4 | 0.157 ± 0.163 | 97.4% | 43.8% |

Embodiment 12

20 mg PEG-RAPA and 8 mg RAPA are weighed, and added with 40 mL $CH_2Cl_2$ to be fully dissolved to obtain an organic phase; 120 mL of an aqueous solution containing 2% PVA is taken as an aqueous phase, and then the organic phase is dripped into the aqueous phase with a syringe while performing ultrasound by using probe ultrasound under ice bath conditions, so as to obtain a white emulsion after performing ultrasonic emulsification for 30 min. The organic solvent is removed by a rotary evaporator at 40° C., and centrifuged at 4000 r/min for 5 min to remove unencapsulated drugs and larger particles for taking a supernatant, so as to obtain the PEGylated rapamycin nanoparticle solution.

The particle size and PDI of the PEGylated rapamycin nanoparticle solution are determined by DLS method.

100 μL PEGylated rapamycin nanoparticle solution is taken, added with acetonitrile until the volume reaches 1 mL, and then is subjected to ultrasound for 20 min to destroy the nanoparticle structure, so that the rapamycin is released free into the solution; then the solution is centrifuged at 12000 r/min for 10 min for taking a supernatant, which is filtered by 0.22 μm microporous membrane; finally, a concentration of RAPA is determined by HPLC analysis, and an encapsulation efficiency and a drug loading of the PEGylated rapamycin nanoparticle are determined.

The test results are shown in Table 3.

TABLE 3

Test Results of PEGylated Rapamycin Nanoparticle

| Particle size (nm) | PDI | Encapsulation efficiency | Drug loading |
|---|---|---|---|
| 115.1 ± 6.3 | 0.197 ± 0.032 | 94.7% | 50.0% |

4. Preparation of Freeze-dried Powder Injection of PEGylated Rapamycin Nanoparticle Embodiment 13

The PEGylated rapamycin nanoparticle solution prepared according to Embodiments 10 to 12 is centrifuged at 12000 r/min for 45 min for removing a supernatant and removing PVA, and then after the precipitate is resuspended with ultrapure water, a concentrated nanoparticle aqueous solution is obtained. 2 mL nanoparticle aqueous solution is taken into 10 mL penicillin vial respectively, and added with a freeze-drying protective agent (with a mass fraction of 5%) for freeze-drying.

(1) Preparation of Freeze-Dried Powder Injection of PEGylated Rapamycin Nanoparticle Using Different Freeze-Drying Protective Agents The mass fraction of the freeze-drying protective agent is 5%. 0.1 g of freeze-drying protective agent is taken into 10 mL penicillin vial, and dissolved using 2 mL PEGylated rapamycin nanoparticle aqueous solution respectively for freeze-drying. The appearance, the reconstitution speed and the clarity of the prepared freeze-dried powder injection of nanoparticle are observed, and the particle size and PDI of the reconstituted nanoparticle are determined.

The evaluation on quality for the preparation of freeze-dried powder injection of PEGylated rapamycin nanoparticle using different freeze-drying protective agents is shown in Table 4.

TABLE 4

Preparation of Freeze-dried Powder Injection of PEGylated Rapamycin Nanoparticle Using Different Freeze-drying Protective Agents

| Freeze-drying protective agent | Appearance | Reconstitution Speed | Clarity | Particle size (nm) | PDI |
|---|---|---|---|---|---|
| 5% Lactose | +++ | +++ | ++ | 186.6 | 0.212 |
| 5% Sucrose | ++ | +++ | ++ | 181.3 | 0.230 |
| 5% Mannitol | +++ | + | + | 190.2 | 0.421 |
| 1.25% Lactose + 3.75% Sucrose | ++ | +++ | +++ | 173.1 | 0.250 |
| 2.5% Lactose + +2.5% Sucrose | ++ | +++ | +++ | 185.0 | 0.251 |
| 3.75% Lactose + +1.25% Sucrose | +++ | +++ | +++ | 170.4 | 0.217 |
| 4.5% Lactose + +0.5% Sucrose | +++ | +++ | ++ | 185.9 | 0.213 |

Notes:
1. Appearance: +severe shrinkage and collapse, unable to fall off completely; ++partial shrinkage and collapse, slightly sticking to the wall; +++no shrinkage and collapse, able to fall off in one piece.
2. Reconstitution speed: +require ultrasound for 1 min for complete reconstitution, ++require ultrasound for 30 s for complete reconstitution, +++immediate reconstitution.
3. Clarity: +poor opalescence, obvious turbidity; ++some opalescence, with a little turbidity; +++obvious opalescence without turbidity.

(2) Preparation of Freeze-Dried Powder Injection of PEGylated Rapamycin Nanoparticle Using Different Pre-Freezing Temperatures The freeze-dried powder injection of PEGylated rapamycin nanoparticle is prepared under pre-freezing temperatures of −35° C. and −45° C. respectively. The appearance, the reconstitution speed and the clarity of the prepared freeze-dried powder injection of nanoparticle are observed, and the particle size and PDI of the reconstituted nanoparticle are determined.

The evaluation on quality for the preparation of freeze-dried powder injection of PEGylated rapamycin nanoparticle using different pre-freezing temperatures is shown in Table 5.

TABLE 5

| Preparation of Freeze-dried Powder Injection of PEGylated Rapamycin Nanoparticle Using Different Pre-freezing Temperatures | | | | | |
|---|---|---|---|---|---|
| Pre-freezing temperature (° C.) | Appearance | Reconstitution Speed | Clarity | Particle size (nm) | PDI |
| −45 | ++ | +++ | +++ | 177.5 | 0.250 |
| −35 | ++ | +++ | +++ | 185.8 | 0.217 |

Notes:
1. Appearance: +severe shrinkage and collapse, unable to fall off completely; ++partial shrinkage and collapse, slightly sticking to the wall; +++no shrinkage and collapse, able to fall off in one piece.
2. Reconstitution speed: +require ultrasound for 1 min for complete reconstitution, ++require ultrasound for 30 s for complete reconstitution, +++immediate reconstitution.
3. Clarity: +poor opalescence, obvious turbidity; ++some opalescence, with a little turbidity; +++obvious opalescence without turbidity.

(3) Preparation of Freeze-Dried Powder Injection of PEGylated Rapamycin Nanoparticle Using Different Pre-Freezing Methods The freeze-dried powder injection of PEGylated rapamycin nanoparticle is prepared by using fast freezing method and slow freezing method respectively. The appearance, the reconstitution speed and the clarity of the prepared freeze-dried powder injection of nanoparticle are observed, and the particle size and PDI of the reconstituted nanoparticle are determined.

The evaluation on quality for the preparation of freeze-dried powder injection of PEGylated rapamycin nanoparticle using different pre-freezing methods is shown in Table 6.

TABLE 6

| Preparation of Freeze-dried Powder Injection of PEGylated Rapamycin Nanoparticle Using Different Pre-freezing Methods | | | | | |
|---|---|---|---|---|---|
| Pre-freezing method | Appearance | Reconstitution speed | Clarity | Particle size (nm) | PDI |
| Fast freezing | ++ | +++ | +++ | 170.6 | 0.160 |
| Slow freezing | ++ | +++ | ++ | 190.7 | 0.226 |

Notes:
1. Appearance: +severe shrinkage and collapse, unable to fall off completely; ++partial shrinkage and collapse, slightly sticking to the wall; +++no shrinkage and collapse, able to fall off in one piece.
2. Reconstitution speed: +require ultrasound for 1 min for complete reconstitution, ++require ultrasound for 30 s for complete reconstitution, +++immediate reconstitution.
3. Clarity: +poor opalescence, obvious turbidity; ++some opalescence, with a little turbidity; +++obvious opalescence without turbidity.

5. Test on Anti-Urate-Oxidase Antibody-Reducing Effects in Mice Through Combined Administration of Two Rapamycin Nanoparticles with Urate Oxidase

Embodiment 14

The materials used in the test are: the PEGylated rapamycin nanoparticle prepared in the invention (particle size of nanoparticle of 160.4 nm, and content of rapamycin of 663.8 μg/vial); the rapamycin PLGA nanoparticle (particle size of nanoparticle of 170.5 nm, and content of rapamycin of 294.8 g/vial); recombinant candida urate oxidase (content of 0.72 mg/mL*7 mL/vial), from Shenyang R&D Center of Shenyang 3sbio Inc.

45 mice are randomly divided into 3 groups according to body weight, 15 mice in each group. The groups and doses are shown in Table 7.

TABLE 7

| Pharmacodynamic Test Dosage Table | | | | | |
|---|---|---|---|---|---|
| Groups | | Dose mg/kg | Concentrations mg/mL | Volume mL/kg | Injection dose mL/piece |
| 1 | Urate oxidase control group | 7.2 | 0.72 | 10 | 0.2 |
| 2 | PEGylated rapamycin polymer nanoparticle + Urate oxidase | 1.44 + 7.2 | 0.144 + 0.72 | 20 | 0.4 |
| 3 | PLGA-loaded rapamycin nanoparticle + urate oxidase | 1.44 + 7.2 | 0.144 + 0.72 | 20 | 0.4 |

Group 1, group 2, and group 3 are administered twice a week for 4 consecutive weeks (according to the detection results on anti-urate-oxidase antibody, the administration period may be extended), and each group was administered intravenously to mice. Urate oxidase is mixed with the nanoparticle for administration in groups 2 and 3 before administration.

About 5 days after the last administration, 0.5 mL of mouse whole blood is collected in a non-anticoagulant tube, and the serum is separated and frozen for detection of anti-urate-oxidase antibodies.

The detection results on anti-urate-oxidase antibody are shown in Tables 8 and 9.

TABLE 8

| Titers of anti-urate-oxidase antibodies after 4 weeks of administration | | | | | |
|---|---|---|---|---|---|
| Group 1 | | Group 2 | | Group 3 | |
| Sample No. | Titer | Sample No. | Titer | Sample No. | Titer |
| 1 | 1:6250 | 16 | — | 31 | 1:1250 |
| 2 | 1:6250 | 17 | — | 32 | 1:1250 |
| 3 | 1:6250 | 18 | — | 33 | 1:6250 |
| 4 | 1:6250 | 19 | — | 34 | 1:250 |
| 5 | 1:6250 | 20 | — | 35 | 1:6250 |
| 6 | 1:1250 | 21 | — | 36 | 1:1250 |
| 7 | 1:1250 | 22 | — | 37 | 1:1250 |
| 8 | 1:31250 | 23 | — | 38 | 1:6250 |
| 9 | 1:6250 | 24 | — | 39 | 1:6250 |
| 10 | 1:6250 | 25 | 1:250 | 40 | 1:6250 |
| 11 | N/A | 26 | — | 41 | 1:6250 |
| 12 | 1:6250 | 27 | — | 42 | 1:6250 |
| 13 | 1:250 | 28 | — | 43 | 1:1250 |
| 14 | 1:6250 | 29 | — | 44 | 1:6250 |
| 15 | 1:6250 | 30 | — | 45 | 1:1250 |

Mice in each group are administered by tail vein injection (the gray background indicates that when the tail vein could not be administered, the injection way is changed to intraperitoneal injection for 1-2 times per mouse) for 4 weeks (8 times), wherein Group 2 (PEGylated rapamycin polymer nanoparticle+urate oxidase) has the smallest titer of anti-urate-oxidase antibodies, and Group 3 (PLGA-loaded rapamycin nanoparticle+urate oxidase) is not significantly better than Control Group 1 (urate oxidase control group).

TABLE 9

| Titers of anti-urate-oxidase antibodies after 6 weeks of administration | | | | | |
|---|---|---|---|---|---|
| Group 1 | | Group 2 | | Group 3 | |
| Sample No. | Titer | Sample No. | Titer | Sample No. | Titer |
| 1 | 1:6250 | 16 | — | 31 | 1:1250 |
| 2 | 1:1250 | 17 | — | 32 | 1:1250 |
| 3 | 1:31250 | 18 | — | 33 | 1:6250 |
| 4 | 1:6250 | 19 | — | 34 | 1:250 |
| 5 | 1:1250 | 20 | 1:50 | 35 | 1:6250 |
| 6 | 1:6250 | 21 | — | 36 | 1:6250 |
| 7 | 1:1250 | 22 | — | 37 | 1:1250 |
| 8 | 1:31250 | 23 | — | 38 | 1:6250 |
| 9 | 1:6250 | 24 | — | 39 | 1:6250 |
| 10 | 1:6250 | 25 | 1:250 | 40 | 1:1250 |
| 11 | 1:31250 | 26 | — | 41 | 1:6250 |
| 12 | 1:1250 | 27 | — | 42 | 1:1250 |
| 13 | 1:250 | 28 | — | 43 | 1:1250 |
| 14 | 1:6250 | 29 | — | 44 | 1:6250 |
| 15 | 1:6250 | 30 | — | 45 | 1:1250 |

Mice in each group are administered by tail vein injection (the gray background indicates that when the tail vein could not be administered, the injection way is changed to intraperitoneal injection, and the injection should be administered no more than 5 times per mouse) for 6 weeks (12 times), wherein the results are basically the same as those under 4 weeks of administration, and Group 3 has 3 mice with increased titers of antibody.

The combined administration of urate oxidase protein and PEGylated rapamycin nanoparticle may effectively prevent the production of anti-urate-oxidase antibodies in mice, with effects obviously better than the combined administration of urate oxidase protein and rapamycin PLGA nanoparticle.

The preferred embodiments of the present invention disclosed above are only used to help the description of the present invention. The preferred embodiments do not describe all the details, and are not intended to limit the invention only to be the specific embodiments. It is obvious that various modifications and changes can be made to the content of the specification. The present invention selects and specifically describe the embodiments with the purpose of better explain the principle and practical use of the present invention, such that a person skilled in the art can well understand and utilize the present invention. The present invention is merely limited by the appended claims and the scope and equivalents thereof.

What is claimed is:

1. A concomitant drugs, comprising:

PEGylated rapamycin nanoparticles comprising a therapeutically effective dose of a PEGylated rapamycin compound represented in formula (I), wherein n is 10-150;

Formula (I)

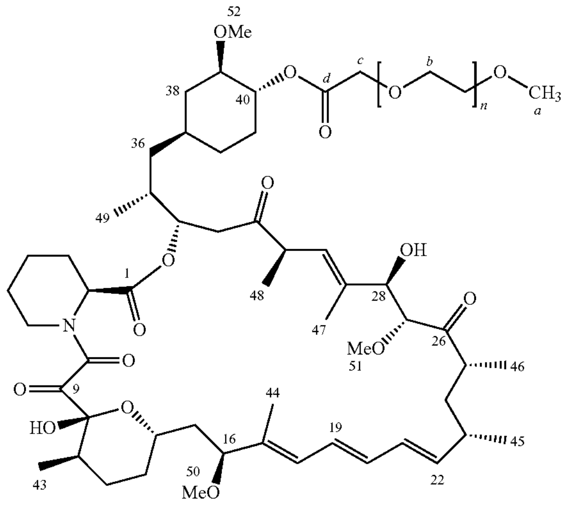

a urate oxidase; and a pharmaceutically acceptable carrier.

* * * * *